United States Patent [19]
Cohen et al.

[11] Patent Number: 6,001,875
[45] Date of Patent: Dec. 14, 1999

[54] IN VIVO METHODS OF TREATMENT TO PREVENT KIDNEY DYSFUNCTION USING SUBSTANCES THAT INHIBIT ALBUMIN GLYCATION

[75] Inventors: Margo P. Cohen, NY, N.Y.; Rex Clements, Piveville, Pa.

[73] Assignee: Exocell, Inc., Philadelphia, Pa.

[21] Appl. No.: 09/015,148

[22] Filed: Jan. 29, 1998

Related U.S. Application Data

[63] Continuation-in-part of application No. 08/650,229, May 20, 1996, which is a continuation-in-part of application No. 08/603,147, Feb. 20, 1996, abandoned.

[51] Int. Cl.⁶ .................................................... A67K 31/24
[52] U.S. Cl. ............................................................ 514/534
[58] Field of Search ............................................... 514/534

[56] References Cited

U.S. PATENT DOCUMENTS 4,060,626  11/1977  Hrstka et al. ............................ 424/274
5,245,046   9/1993  Youngdale et al. ..................... 548/495

OTHER PUBLICATIONS

EMbase Abstract 92126412 (1992) •van Boekel et al, 1992.

*Primary Examiner*—Zohreh Fay
*Attorney, Agent, or Firm*—Caesar, Rivise, Bernstein, Cohen & Pokotilow Ltd.

[57] ABSTRACT

The present invention is directed to the prevention in vivo of the nonenzymatic glycation of albumin, which generates biologically active Amadori glucose adducts in the albumin molecule, as well as methods of using compounds that protect against nonenzymatic glycation in vivo to treat kidney dysfunction.

8 Claims, No Drawings

IN VIVO METHODS OF TREATMENT TO PREVENT KIDNEY DYSFUNCTION USING SUBSTANCES THAT INHIBIT ALBUMIN GLYCATION

RELATED APPLICATIONS

This application is a continuation-in-part of pending application Ser. No. 08/650,229, filed May 20, 1996 now pending which was a continuation-in-part of application Ser. No. 08/603,147, filed Feb. 20, 1996 now abandoned, the entire disclosures of which are incorporated by reference herein.

TECHNICAL FIELD OF INVENTION

This invention is related to the discovery that certain compounds with albumin-binding properties can inhibit nonenzymatic glycation of albumin in vivo. The invention further relates to the ability of such compounds to prevent kidney dysfunction manifest by increased urine albumin excretion.

BACKGROUND OF THE INVENTION

Nonenzymatic glycation of albumin is a condensation reaction between glucose and reactive epsilon amino groups of lysine residues in the protein. The reaction is initiated with attachment of the aldehyde function of acyclic glucose to albumin via nucleophilic addition, forming an aldimine, also known as a Schiff base. This intermediate undergoes an Amadori rearrangement to form an amino-deoxyfructose derivative (fructosyllysine) in stable ketoamine linkage. The Amadori product may give rise to a heterogeneous group of poorly defined advanced glycation end products (AGE), the formation of which is believed to evolve through various rearrangement, dehydration, oxidation and polymerization reactions. Prior art has suggested a pathophysiologic role of AGE-modified protein in disorders associated with aging and with diabetes, and that inhibition of AGE-crosslink formation might be beneficial in the treatment of such disorders (Brownlee et al, *Science* 232:1629, 1986; *New Engl J Med* 318:1315, 1988; Vlassara, *J Lab Clin Med* 124:19, 1994). However, recent experimental work indicates that albumin modified by Amadori glucose adducts is an important pathogenetic factor in the development of kidney and vascular dysfunction in aging and in diabetes. Glycated albumin exists in vivo principally as the Amadori product and its concentration is driven by the ambient glucose concentration to which albumin is exposed during its residence time in the circulation. Glycated albumin normally constitutes about 1–2% of total plasma albumin, and may be increased one-and-a-half to three fold in diabetes (Cohen and Hud, *J Immunol Meth* 122;279, 1989).

Experimental studies have shown that Amadori-modified glycated albumin has distinct biologic effects that non-glycated albumin does not possess. These glycated albumin-induced effects, which include stimulation of matrix production by kidney and vascular cells, mimic the changes associated with glomerulosclerosis and vasculopathies, are likely mediated by ligand-receptor systems for the glucose-modified epitope in the glycated protein, and can be prevented by molecules capable of reacting with the Amadori adduct in glycated albumin (Ziyadeh and Cohen, *Molec Cell Biochem* 125:19, 1993; Cohen et al, *Molec Cell Biochem* 151:61, 1995; *J Clin Invest* 95:2338, 1995; Cohen and Ziyadeh, *Kidney Int* 45:475, 1995; Wu and Cohen, *Biochem Biophys Res Comm* 207:521, 1995). Such molecules may be monoclonal antibodies or other compounds which specifically bind to the fructosyllysine epitope present on glycated albumin but not present on non-glycated albumin, and which are disclosed in U.S. Pat. No. 5,223,392 and U.S. Pat. No. 5,518,720.

The deleterious biologic effects of glycated albumin make it desirable to have the means to prevent the attachment of glucose to albumin lysine-amino groups and thereby lower glycated albumin concentrations. Such means would beneficially influence the development of kidney and vascular dysfunction in aging and in diabetes by mechanisms different from those disclosed in the prior art, which are designed to neutralize the biologic effects of glycated albumin. One manner by which lowering of glycated albumin concentrations could be accomplished in people with diabetes would be with intensive regimens for control of blood glucose levels. The Diabetes Control and Complications Trial showed that reducing the concentration of glycated protein in the circulation with intensive insulin therapy lowers the risk for development of nephropathy and retinopathy (*New Engl J Med* 329:977, 1993). However, it is widely appreciated that implementation and maintenance of intensive regimens such as those used in the DCCT are difficult and may be risky, and that the majority of diabetic patients remain significantly hyperglycemic with current antidiabetic therapies. Further, such regimens do not apply to non-diabetic people at risk for kidney or vascular disease. Another means by which lowering of glycated albumin concentrations could be achieved is with compounds that prevent condensation of glucose with lysine amino groups. Acetylsalicylic acid (aspirin), by virtue of rapid acetylation of epsilon amino groups, can competitively inhibit this reaction (Rao and Cotlier, *Biochem Biophys Res Comm* 151:991, 1977; Rendell et al, *J Lab Clin Med* 107:286, 1986). However, the impact of widespread protein acetylation is unknown. Moreover, the glycation-inhibiting activity of aspirin is relatively weak and potential therapeutic benefits that might be ascribed to this activity are limited by the rapid hydrolysis and short half-life of acetylsalicylic acid in the blood and by side effects anticipated at doses required to inhibit glycation in vivo (Costello and Green, *Arth Rheum* 25:550, 1982; Rowland and Riegelman, *J Phann Sci* 57:1313, 1968). Other compounds which lack acetyl groups but bind to albumin in a manner that effectively interferes with the condensation of glucose with free lysine amino groups would be more desirable as glycation inhibitors.

In an in vitro experiment van Boekel et al (*Biochim Biophys Acta* 1120:201, 1991) reported that 2,benzene acetic acid in concentrations of 1–5 mM could reduce the amount of sugar-attached protein after incubation of commercially purchased powdered albumin with 5 mM glucose-6-phosphate. However, the concentration of the compound required to inhibit sugar attachment in vitro, and the composition and concentration of the sugar substance used to glycate the protein, do not represent in vivo conditions. Therefore, the conclusion from this study is that the compound would not be effective in inhibiting albumin glycation in vivo since the primary sugar present in the circulation is glucose, and since the concentrations of the compound required to inhibit glycation in vitro would be toxic if given to living subjects. Additionally, van Boekel et al concluded that, because the compound binds to albumin, its concentration in tissues would be too low to be of import in disease states if administered in vivo. Van Boekel et al did not perform any in vivo experiments. The van Boekel et al study does not afford any evidence that the compound could affect glycation in vivo, and contra-indicates the possibility that in vivo administration of therapeutically acceptable amounts of the compound could lower glycated albumin concentrations in living human subjects or could beneficially influence kidney or vascular dysfunction in either diabetic or non-diabetic people.

It is well known that nonenzymatic glycation under in vitro conditions does not represent that which occurs in vivo with respect to the number and nature of glycatable sites (c.f. Cohen, Diabetes and Protein Glycosylation, Springer Verlag, 1986, p.12; Diabetes and Protein Glycation, JC Press, 1996, pp. 8–9). It also is well known that although various reducing sugars such as glucose-6-phosphate can condense with protein amino groups in vitro, the concentrations required vastly exceed those found of such sugars in vivo, and that such reducing substances promote glycation that is not representative in chemistry or in nature of that which occurs in vivo. These facts lead one to conclude that the effect of diclofenac on the attachment of glucose-6-phosphate at 5 mM concentration in vitro cannot be extrapolated to the in vivo situation where glucose-6-phosphate resides intracellularly and at a lesser order of magnitude of concentration. Further, diclofenac is usually administered in daily amounts of 100–200 mg, and van Boekel et al required concentrations of 1–5 mM to achieve any inhibition of the binding of glucose-6-phosphate to albumin in vitro. The peak plasma levels of diclofenac obtainable after a dose of 100–200 mg are 1–2 ug/ml. This concentration is equivalent to 3–6 uM, which is 1000-fold less than the concentration found by van Boekel et al to be necessary to inhibit albumin glycation in vitro. These facts lead one to conclude that diclofenac would be clinically useless for inhibition of albumin glycation in vivo, since the amount required by van Boekel et al to be effective in vitro would be toxic and deleterious if administered in vivo to living subjects. Additionally, van Boekel et al emphasize that AGE, not Amadori products, are important in glycation-related disease affecting the kidneys and eyes, leading one to conclude that reducing glycated albumin per se would be without salutary effect in vivo on kidney function or in other vascular disorders. In short the available art indicates that the in vivo administration of therapeutic amounts of compounds such as diclofenac would be useless either for the purpose of lowering concentrations of glycated albumin in living subjects or for treating kidney dysfunction.

The present invention discloses the novel and unexpected discovery that therapeutically acceptable amounts of diclofenac inhibit the formation of glycated albumin in vivo and prevent the development of kidney dysfunction in living subjects.

SUMMARY OF THE INVENTION

The present invention provides a means of preventing the nonenzymatic glycation of albumin in living subjects.

The present invention also provides a novel method for preventing the in vivo formation of biologically active Amadori glucose adducts in the albumin molecule.

Additionally, the present invention provides a novel method for limiting the in vivo generation of biologically active glycated albumin epitopes for interaction with their cell-associated receptors.

The present invention is achieved with compounds capable of binding to albumin in such a way as to inhibit the reaction of glucose with lysine amino groups in the protein.

The present invention also provides a method for treating kidney and vascular dysfunction in human subjects.

The present invention further provides a method for preventing kidney dysfunction manifested by microalbuminuria.

Another embodiment of the present invention provides a method for treating kidney dysfunction in aging and diabetes comprising the step of administering to a patient a therapeutic molecule capable of preventing the nonenzymatic glycation of albumin in vivo.

Another embodiment of the present invention provides a method for treating kidney dysfunction in aging and diabetes comprising the step of administering a therapeutic molecule capable of preventing the formation of biologically active Amadori glucose adducts in the albumin molecule.

The present invention thus relates to use of compounds that are reactive in vivo with domain(s) in human albumin and that, by binding to these sites in the structure of albumin, protect the protein against nonenzymatic glycation in vivo.

DETAILED DESCRIPTION

It is a finding of the present invention that compounds that bind to human albumin protect the protein from nonenzymatic glycation. This protective action reduces the amount of glycated albumin containing Amadori glucose adducts that is formed upon exposure of the protein to glucose in the circulation in vivo. On the basis of this finding, methods are provided for the treatment of kidney dysfunction and vascular disorders. Diabetics display increased levels of glycated albumin in their plasma. This increase is pathogenetically involved in the development of kidney and vascular disease. Non-diabetic people have significant amounts of glycated albumin in the circulation, which also can promote kidney and vascular dysfunction. The present invention lowers the glycated albumin concentration. A decrease in the plasma glycated albumin concentration results in amelioration of pathologic changes in the kidney and in prevention of a decline in kidney function. Protection of albumin from nonenzymatic glycation decreases the amount of glycated albumin ligand available for binding to receptors that are present on kidney and vascular cells and that mediate the biologic effects of glycated albumin, such as stimulation of extracellular matrix production.

Compounds which can be administered to humans for these therapeutic uses include those which are capable of binding to sites in the tertiary structure of albumin, which can involve different parts of the primary structure of the protein and which encompass a lysine residue that is a preferential site of nonenzymatic glycation in vivo. One such compound is 2-benzene acetic acid (diclofenac).

Diclofenac has been used as a nonsteroidal anti-inflammatory agent. It is a weak acid (pKa=4) that is virtually completely absorbed from the gastrointestinal tract with peak levels of approximately 2 ug/ml achieved 2–3 hours after dosing. The usual recommended dose is 100–200 mg/day in divided doses. After absorption, more than 99% of absorbed compound is bound to the circulating albumin (Chan et al, *J Pharm Sci* 76:105, 1987). Fluorescent marker displacement analysis indicates that His 146 and Lys 195 residues in albumin are involved in a high affinity binding site for diclofenac, and that there is another binding site, involving a different part of the primary structure of albumin, in which Lys 199 plays a role (Chamouard et al, *Biochem Pharmacol* 34:1695, 1985). Lys 199 represents a fatty acid binding site, suggesting that dissociation of fatty acid from albumin renders this site available for diclofenac binding. Lysine 199 also serves as one of the preferential sites for nonenzymatic glycation in vivo (Garlick et al, *J Biol Chem* 258:6142, 1983). The principal site of albumin glycation in vivo is lysine 525, which accounts for about 33% of the overall glycation of this protein (Fluckiger, *Mono-* graphs in *Atherosclerosis* 13:53, 1985; Iberg et al, *J Biol Chem* 261:13542, 1986), and which also may bind diclofenac. Lysine 525 modified by Amadori glucose adducts comprises the epitope recognized by cell associated receptors for glycated albumin, and protection by diclofenac of this residue inhibits this ligand-receptor binding.

For treatment and preventative purposes, therapeutic molecules, as described above, can be administered to block glycatable sites in albumin. By binding to such sites, the therapeutic molecules can prevent the formation of Amadori glucose adducts in albumin and protect against tissue damage which is caused by circulating glycated albumin and its binding to cell recognition sites.

Administration according to the methods of the present invention is any method which achieves a sufficient concentration of therapeutic molecule in the circulation or targeted region of the body to be therapeutically useful. Typically such administration will be oral, although parenteral injection may also be used. Typical doses of therapeutic molecules will achieve effective concentrations of albumin-binding power. In the present invention administration of diclofenac encompasses doses of 100–300 mg/day.

The above disclosure generally describes the present invention. A more complete understanding can be obtained by reference to the following specific examples which are provided herein for purposes of illustration only, and are not intended to limit the scope of the invention.

EXAMPLE 1

In vivo Inhibition of Albumin Glycation

Plasma samples were obtained from six human subjects at the initiation and termination of 28 days of treatment with diclofenac, 180 mg/day orally in divided doses. The concentration of glycated albumin in these samples was determined by analysis in an enzyme linked immunoassay (ELISA) which uses monoclonal antibodies known to specifically react with epitopes containing Amadori-glucose adducts that are found on native glycated albumin but that are not found on nonglycated albumin. The antibodies bind fructosyllysine residues from the group consisting of lys 195, lys 199, lys 281, lys 439 and lys 525 in the albumin molecule. As shown in Table 1, administration of diclofenac produced a 32% reduction in the amount of circulating glycated albumin.

TABLE I

| Sample | mg/ml Glycated Albumin |
| --- | --- |
| Baseline | 1.86 |
| Post-treatment | 1.27 |
| Change | (−32%) |

EXAMPLE 2

Lowering Glycated Albumin Prevents Kidney Dysfunction

Urine samples were obtained from six human subjects at the initiation and termination of 28 days of treatment with diclofenac, 180 mg/day orally in divided doses. Urine albumin excretion was measured by ELISA and normalized to urine creatinine concentration. Increased urine albumin (microalbuminuria) is the established hallmark of early kidney dysfunction. As shown in Table 2, administration of diclofenac produced a 52% reduction in microalbuminuria.

TABLE 2

| Sample | Urine Albumin ug/mg creatinine |
| --- | --- |
| Baseline | 60.6 |
| Post-treatment | 26.6 |
| Change | (−52%) |

What is claimed is:

1. A method of treating a living being having kidney dysfunction which is caused by glycated albumin in serum of the living being comprising the steps of: administering in a therapeutically acceptable carrier to the living being a therapeutically effective amount of diclofenac which protects against nonenzymatic glycation of albumin and lowers the living being's serum concentration of glycated albumin.

2. The method of claim 1 wherein diclofenac inhibits the formation of Amadori glucose adducts in the albumin molecule.

3. The method of claim 2 wherein fructosyllysine modification of albumin occurs at one or more residues selected from the group consisting of lysine 199, lysine 195, lysine 281, lysine 439 and lysine 525.

4. The method of claim 1 wherein diclofenac inhibits the formation of biologically active glycated albumin epitopes for binding to cell-associated receptors.

5. The method of claim 1 wherein the living being has kidney dysfunction and is at risk for kidney dysfunction, as manifest by elevated urine albumin excretion.

6. A method of lowering serum concentrations of glycated albumin in a living being with kidney dysfunction or at risk for kidney dysfunction comprising the step of administering to the living being a therapeutically effective amount of diclofenac.

7. A method of protecting a living being with kidney dysfunction or at risk for kidney dysfunction from nonenzymatic glycation of albumin comprising the step of administering to the living being a therapeutically effective amount of diclofenac.

8. A method of treating a living being having kidney dysfunction which is caused by glycated albumin in the serum of the living being comprising the steps of: administering a therapeutically effective amount of diclofenac of about 200 mg/day to the living being which protects against the nonenzymatic glycation of albumin in vivo and lowers the living being's serum concentration of glycated albumin.

* * * * *